(12) United States Patent
Fujiwara et al.

(10) Patent No.: US 6,902,806 B2
(45) Date of Patent: Jun. 7, 2005

(54) MESOPOROUS SILICA HAVING CONTROLLED-RELEASE ON-OFF CONTROL FUNCTION, PRODUCTION METHOD THEREOF AND METHOD USING SAME

(75) Inventors: Masahiro Fujiwara, Osaka-fu (JP); Nawal Kishor Mal, Tokyo-to (JP); Yuko Tanaka, Hyogo-ken (JP)

(73) Assignee: National Institute of Advanced Science and Technology, Tokyo (JP)

( * ) Notice: Subject to any disclaimer, the term of this patent is extended or adjusted under 35 U.S.C. 154(b) by 89 days.

(21) Appl. No.: 10/421,697

(22) Filed: Apr. 24, 2003

(65) Prior Publication Data

US 2003/0203206 A1 Oct. 30, 2003

(30) Foreign Application Priority Data

Apr. 30, 2002 (JP) ..................................... 2002-127987

(51) Int. Cl.$^7$ ................................................ B32B 5/16
(52) U.S. Cl. ........................ 428/402; 428/403; 423/335
(58) Field of Search ................................ 428/402, 403; 423/335

(56) References Cited

U.S. PATENT DOCUMENTS

| | | | |
|---|---|---|---|
| 5,026,342 A | | 6/1991 | Hammerstedt et al. |
| 5,922,299 A | * | 7/1999 | Bruinsma et al. ............ 423/335 |
| 6,027,666 A | * | 2/2000 | Ozin et al. ............ 252/301.4 R |
| 6,174,512 B1 | * | 1/2001 | Kosuge et al. ............... 423/705 |
| 6,630,170 B2 | * | 10/2003 | Balkus et al. ................ 424/489 |
| 6,696,258 B1 | * | 2/2004 | Wei et al. ...................... 435/7.2 |
| 6,713,643 B2 | * | 3/2004 | Pinnavaia et al. ........... 556/450 |

FOREIGN PATENT DOCUMENTS

| | | |
|---|---|---|
| DE | 100 21 165 A | 11/2001 |
| WO | WO 99 36357 | 7/1999 |
| WO | WO 00 51724 | 9/2000 |

OTHER PUBLICATIONS

EP Search Report completed Aug. 25, 2003 for App. No. EP 03 25 2709.

Database EMBASE Online! Elsevier Science Publishers, Amsterdam, NL; Aug. 7, 1999 Zhao X S et al: "A novel method for tailoring the pore–opening size of MCM–41 materials" Database accession No. EMB–1999278125 XP002251458 *abstract* & Chemical Communications United Kingdom, vol. 5, No. 15, p.p. 1391–1392 ISSN: 1359–7345.

Vallet–Regi M et al: "A New Property of MCM–41: Drug Delivery System" Chemistry of Materials, American Chemical Society, Washington, US, vol. 13, No. 2, Feb. 1, 2001, p.p. 308–311, XP00105172 ISSN: 0897–4756 *the whole document*.

Database MEDLINE Online!US National Library of Medicine (NLM), Bethesda, MD, US; Jan. 23, 2003 Mal Nawal Kishor et al: "Photocontrolled reversible release of guest molecules from coumarin–modified mesoporous silicia." Database accession No. NLM12540896 XP002251459 *abstract* & Nature. England, vol. 421, No. 6921, p.p. 350–353, ISSN: 0028–0836.

Database BIOSIS Online! Biosciences Information Service, Philadelphia, PA, US; Apr. 16, 2003 Lai Cheng–Yu et al: . "A mesoporous silicia nanosphere–based carrier system with chemically removable CdS nanoparticle caps for stimuli–responsive controlled release of neurotransmitters and drug molecules>" Database accession No. PREV200300306683 XP002251460 *abstract* & Journal of the American Chemical Society, vol. 125, No. 15, p.p. 4451–4459, ISSN: 0002–7863.

B. Munoz: "MCM–41 Organic Modification as drug delivery rate regulator" Chemistry of Materials, American Chemical Society, vol. 15, 2003, p.p. 500–503, XP002251472 Washington, US *the whole document*.

* cited by examiner

Primary Examiner—H. Thi Le
(74) Attorney, Agent, or Firm—Sughrue Mion, PLLC

(57) ABSTRACT

The present invention provides a hexagonal mesoporous silica comprising a photo-dimerizable organic functional group provided at the entrances of the pores thereof, and a hexagonal mesoporous silica comprising a functional substance filled in the pores thereof and a dimerized organic functional group provided at the entrances of the pores to close the entrances. These hexagonal mesoporous silicas allow a substance incorporated therein to be controllably released. The present invention also provides a method of producing the mesoporous silica, and a method using the mesoporous silica to control the release of a functional substance incorporated therein.

15 Claims, No Drawings

MESOPOROUS SILICA HAVING CONTROLLED-RELEASE ON-OFF CONTROL FUNCTION, PRODUCTION METHOD THEREOF AND METHOD USING SAME

FIELD OF THE INVENTION

The present invention relates to a novel mesoporous silica having a hexagonal pore structure modified with an organic functional group, a production method thereof, and use thereof.

BACKGROUND OF THE INVENTION

In recent years, incorporating a chemical substance into a solid material and gradually or controllably releasing the chemical substance from the inside to the outside of the solid material, a so-called "controlled release system" "sustained release system", is regarded as noteworthy. The controlled release system is intended to provide a supply of various chemical substances having different functions in a necessary amount only when needed. The controlled release system is useful in various industrial fields, such as medicines, agricultural chemicals, cosmetics, catalysts, fertilizers and aroma chemicals. In addition to providing efficient use of chemical substances, the controlled release function is directly related to leading-edge technologies, such as technologies for reducing environmental risks (chemical pollution) and technologies for suppressing side effects in medical care (drug delivery system).

While various techniques have been proposed for a controlled release system, most of them are directed to mixing a chemical substance into a polymer gel or forming a complex consisting of a chemical substance and a polymeric material. These techniques cannot disable the continuous release of a chemical substance, even if they can reduce the rate of the controlled-release of the chemical substance. That is, they cannot provide an on-off control function of controllably releasing a chemical substance in a necessary amount only when needed.

There have also been proposed some controlled release systems having an on-off control function based on a device using an electrode (Japanese Patent Laid-Open Publication Nos. H 05-269373, H 05-261278, H 05-231560, H 05-221469, H 05-221468 and H 05-212277). Since these systems are essentially provided with a power source, an electrode and an interconnection therebetween, to allow a chemical substance to be controllably released according to an electric field signal, they are not applicable in a specific region where the above interconnection cannot be constructed, for example, within a living body. Thus, there is a need for a controlled release system having an on-off control function in the form of a micro self-sustained system independent of a power source and others.

Silica (gel) is widely used because it has almost no harm to the environment and living organisms. As one of features, silica has large pores capable of absorbing and incorporating various kinds of chemical substances therein. While it is contemplated to use silica (gel) in a controlled release system in such a manner that a chemical substance incorporated therein is controllably released therefrom, no on-off control function will be attained if silica (gel) is used as it is.

A technique for providing a controlled-release on-off control function to silica gel or capsule-type silica has been proposed recently (Japanese Patent Laid-Open Publication Nos. 2000-279817, 2001-131249 and 2001-213992). However, an accurate controlled-release control of an incorporated substance cannot be achieved due to uneven size in pores of the silica gel. Thus, there is a need for a material with pores having more uniform outlets or access regions to the outside.

A material fulfilling the above requirement includes hexagonal mesoporous silica, such as MCM-41, having pores with regularity in diameter and configuration. There is a recent report disclosing a spontaneous-diffusion controlled-release property of a drug incorporated in MCM-41 (M. Vallet-Regi et al, Chem. Mater. Vol. 13, p 308, 2001; B. Muñoz et al., Chem. Mater. Vol. 15, p 500, 2003). This report includes no description of controlled-release on-off control.

SUMMARY OF THE INVENTION

In view of the above circumstances, it is a primary object of the present invention to provide a mesoporous silica having a hexagonal structure, capable of controllably releasing a substance incorporated therein, and a production method thereof.

The inventors found that a functional substance could be confined in the pores of a hexagonal mesoporous silica by introducing a dimerizable organic functional group at the entrances of the pores and dimerizing the functional group. The incorporated substance could be released when needed by splitting the dimerized functional group. Based on this knowledge, the inventors have finally accomplished the present invention.

According to a first aspect of the present invention, there is provided a mesoporous silica having a hexagonal structure. This mesoporous silica comprises an organic functional group provided at the entrances of the pores thereof. The organic functional group is dimerizable in response to light.

In the mesoporous silica set forth in the first aspect of the present invention, the organic functional group may be an $\alpha$, $\beta$-unsaturated ketone moiety.

The organic functional group may be reversibly dimerizable in response to light.

The organic functional group may be derived from a coumarin derivative.

According to a second aspect of the present invention, there is provided a mesoporous silica having a hexagonal structure. This mesoporous silica comprises a functional substance filled in the pores thereof, and a dimerized organic functional group provided at the entrances of the pores to close the entrances.

In a first embodiment of the mesoporous silica set forth in the second aspect of the present invention, the organic functional group may be $\alpha$, $\beta$-unsaturated ketone moiety.

In a second embodiment of the mesoporous silica set forth in the second aspect of the present invention, the organic functional group may be reversibly dimerizable in response to light.

In a third embodiment of the mesoporous silica set forth in the second aspect of the present invention, the organic functional group may be derived from a coumarin derivative.

According to a third aspect of the present invention, there is provided a method of producing a mesoporous silica, comprising the steps of (1) preparing a mesoporous silica having a hexagonal structure by use of a template comprising a surfactant capable of forming a hexagonal structure in an aqueous solution, (2) introducing an organic functional group, which is dimerizable in response to light, to the mesoporous silica having a hexagonal structure while leaving the surfactant in the pores of the mesoporous silica, and (3) then removing the surfactant contained in the mesoporous silica with a solvent.

This method may further include the step of subjecting the mesoporous silica to acid treatment between the preparing step (1) and the introducing step (2).

According to a fourth aspect of the present invention, there is provided a method of producing a mesoporous silica, comprising the steps of (1) preparing a mesoporous silica having a hexagonal structure by use of a template comprising a surfactant capable of forming a hexagonal structure in an aqueous solution, (2) introducing an organic functional group, which is dimerizable in response to light, to the mesoporous silica having a hexagonal structure while leaving the surfactant in the pores of the mesoporous silica, (3) removing the surfactant contained in the mesoporous silica with a solvent, (4) filling the pores of the mesoporous silica with a functional substance, and (5) dimerizing the organic functional group with light.

This method may further include the step of subjecting the mesoporous silica to acid treatment between the preparing step (1) and the introducing step (2).

According to a fifth aspect of the present invention, there is provided a method of removing a chemical substance, comprising the steps of preparing the mesoporous silica set forth in the first aspect of the present invention, incorporating the chemical substance into the pores of the mesoporous silica, and dimerizing the organic functional group with light.

According to a sixth aspect of the present invention, there is provided a method of controlling the release of a functional substance, comprising the steps of preparing the mesoporous silica set forth in the second aspect of the present invention, and splitting the dimerized organic functional group to allow the functional substance to be released from the pores.

According to a seventh aspect of the present invention, there is provided a method of controlling the release of a functional substance, comprising the steps of preparing the mesoporous silica set forth in the second embodiment of the second aspect of the present invention, and irradiating the mesoporous silica with a light having a wavelength causing the split of the dimerized organic functional group to allow the functional substance to be released from the pores.

According to an eighth aspect of the present invention, there is provided a method of controlling the release of a functional substance, comprising the steps of preparing the mesoporous silica set forth in the second embodiment of the second aspect of the present invention, irradiating the mesoporous silica with a light having a wavelength causing the split of the dimerized organic functional group to allow the functional substance to be released from the pores, and irradiating the mesoporous silica with a light having a wavelength causing dimerization of the organic functional group to allow the release of the functional substance to be discontinued.

DESCRIPTION OF THE PREFERRED EMBODIMENT

The present invention is directed to a hexagonal mesoporous silica, i.e., a mesoporous silica having a hexagonal structure. The mesoporous silica essentially comprises a dimerizable organic functional group provided at the entrances of the pores thereof. The organic functional group is dimerizable in response to light, i.e., photo-dimerizable. The present invention is also directed to a hexagonal mesoporous silica comprising a functional substance filled in the pores thereof and a photo-dimerized organic functional group provided at the entrances of the pores to close the entrances.

The former mesoporous silica can be obtained through a method comprising the steps of preparing a mesoporous silica having a hexagonal structure by use of a template comprising a surfactant capable of forming a hexagonal structure in an aqueous solution, introducing an organic functional group, which is dimerizable in response to light, at the entrances of the pores of the mesoporous silica having a hexagonal structure, and then removing the surfactant contained in the mesoporous silica with a solvent.

The latter mesoporous silica including a functional substance filled in the pores can be obtained by adding the steps of filling the pores of the mesoporous silica with the functional substance and dimerizing the organic functional group with light, after the step of removing the surfactant in the above method.

[I] Preparation of Hexagonal Mesoporous Silica with Template Surfactant

A crude product of a hexagonal mesoporous silica may be first prepared by use of a template comprising a surfactant, prior to removing the template (This method has already been reported in U.S. Pat. No. 5,143,879, issued Sep. 1, 1992). This crude product can be obtained through any suitable conventional method, for example, using a silica source and a surfactant capable of forming a hexagonal structure in an aqueous solution, as raw materials.

While the surfactant herein may be a typical surfactant for use in a conventional production process for a mesoporous silica having a hexagonal pore arrangement, the present invention is not limited to a specific surfactant, but any other suitable surfactant capable of forming a hexagonal structure in an aqueous solution may be used. Specifically, the surfactant includes: aliphatic quaternary ammonium salts, such as hexadecyltrimethylammonium bromide, hexadecyltrimethylammonium chloride, octadecyltrimethylammonium bromide, decyltrimethylammonium bromide, dodecyltrimethylammonium bromide, hexadecyldimethylethylammonium bromide; aliphatic amine salts, such as hexadecylamine; and alkyl sulfates, such as sodium dodecyl sulfate.

While the silica source herein may be a typical silica source for use in a conventional production process for a mesoporous silica having a hexagonal pore arrangement, the present invention is not limited to a specific silica source, but any other suitable silica source capable of being formed into a mesoporous silica having a hexagonal pore arrangement may be used. For example, the silica source includes sodium silicate, potassium silicate, calcium silicate, tetraethoxysilane, tetramethoxysilane, and tetra-n-propoxysilane.

Both the surfactant and the silica source are used in the form of aqueous solution. These aqueous solutions are prepared individually.

While the concentration of the surfactant in the aqueous solution may be set at any appropriate value depending on the type of the surfactant to form the hexagonal structure, it is typically about 0.2 to 2 M.

Alkaline compounds (such as sodium hydroxide, potassium hydroxide, tetramethylammonium hydroxide) may be added to the surfactant aqueous solution when needed. When added, the amount of alkaline compounds is preferably about 1 to 1.5 molar equivalents with respect to the surfactant.

The concentration of the silica source in the aqueous solution is typically, but not limited to, about 0.5 to 4 M.

These aqueous solutions are mixed by stirring, at a temperature of about 25° C. to 40° C. for about 0.5 to 5 hours.

While the mixing ratio of the surfactant aqueous solution (vol): the silica-source aqueous solution (vol) may be typically set at 1:0.5 to 1:2, the present invention is not limited to such a specific value, but any other suitable mixing ratio allowing the hexagonal structure formed of the template surfactant to be filled with the silica source may be selected.

Then, an inorganic acid such as sulfuric acid, nitric acid, hydrochloric acid, and hypochlorous acid is added to the mixed solution to set the pH of the mixed solution at about 9 to 12, preferably about 10 to 11, and the resulting solution is stirred at a temperature of about 25° C. to 80° C. for about 0.5 to 6 hours. While the concentration of the inorganic acid to be added may be set at about 0.5 to 4 M, preferably about 1 to 3 M, and the amount of the inorganic acid to be added may be set at about 20 to 100 mL, preferably about 50 to 70 mL, per 100 mL of the mixture solution of the surfactant and the silica source, the present invention is not limited to such a specific value, but any other suitable value allowing the pH of the mixed solution to be set approximately in the above desired range may be selected.

After a precipitate is formed, it is filtered and rinsed with water. Then, the deposit is dried at a temperature of about 80 to 130° C., preferably about 90 to 110° C., for about 10 to 40 hours, preferably about 12 to 26 hours to obtain a hexagonal mesoporous silica with the template surfactant.

After the formation of the above precipitate, the precipitate may be directly filtered and dried. Alternatively, the precipitate may be subjected to acid treatment before the filtration.

The acid treatment may be the following method.

The mixture solution containing the precipitate is first left at a temperature of about 80 to 120° C. for 20 to 30 hours. Then, a neutral salt (e.g. sodium chloride, potassium chloride, lithium chloride, sodium bromide, potassium bromide, sodium iodide, or potassium iodide) is added to the mixture solution at about 60 to 90 mol %, preferably about 70 to 80 mol % on the basis of 100% of silica atoms contained in the silica source. Before being added, the salt is preferably dissolved in a small amount of water.

Then, an inorganic acid (such as sulfuric acid, nitric acid, hydrochloric acid, and hypochlorous acid) is added to the mixture solution to set the pH of the mixed solution at about 9 to 12, preferably about 10 to 11. While the concentration of the inorganic acid may be set at about 0.5 to 4 M, preferably about 1 to 3 M, the present invention is not limited to such a specific value, but any other suitable value allowing the pH of the mixed solution to be set in the above desired range may be selected.

Following the addition of the inorganic acid, the mixed solution containing a precipitate formed therein is left at a temperature of about 80 to 120° C. for 20 to 30 hours.

The above acid treatment, i.e., the operation of adding an inorganic acid to the mixed solution to set the pH thereof at about 9 to 12, preferably 10 to 11 and leaving the mixed solution containing the precipitate at a temperature of about 80 to 120° C. for 20 to 30 hours may be repeated. In this case, no salts may be added on and after the second operation.

While the acid treatment may be repeated for any number of times, it is typically 1 to 5 times, preferably 2 to 3 times.

After completion of the acid treatment(s), the resulting precipitate may be filtered and dried in the same way as described above. The acid treatment provides the hexagonal mesoporous silica with enhanced heat stability.

In this way, the mesoporous silica having a hexagonal pore arrangement can be obtained. At this moment, the surfactant remains in the pores of the mesoporous silica. If a dimerizable organic functional group is introduced to the mesoporous silica while the surfactant is still in the pores thereof, the dimerizable organic functional group never enters into the pores, and a mesoporous silica having an excellent controlled release function can be obtained.

[II] Introduction of Dimerizable Organic Functional Group

In order to introduce an organic functional group which is dimerizable in response to light (hereinafter sometimes referred to as "dimerizable functional group") to the mesoporous silica, a compound having a dimerizable functional group (hereinafter sometimes referred to as "dimerizable compound") is used. This compound may be reversibly or irreversibly dimerizable in response to light irradiation such as ultraviolet irradiation, preferably reversibly dimerizable in response to light irradiation.

The dimerizable compound may be an α, β-unsaturated ketone. Specifically, the compound having the organic functional group reversibly dimerizable in response to light irradiation may be a coumarin derivative having at least one substituent, preferably one or two substituents, such as a hydroxyl, amino, carboxyl or ester group [e.g. —CO—OR$^1$ (R$^1$ may be an alkyl group having about 1 to 6 carbon atoms)]. Examples of the reversibly dimerizable compound include 7-hydroxy coumarin, 3,4-dihydroxy coumarin, 4-hydroxy coumarin, and 7-amino-4-methylcoumarin.

The compound having an organic functional group irreversibly dimerizable in response to light radiation may be chalcones having at least one substituent, preferably one or two substituents, such as a hydroxyl, amino, carboxyl or ester group [e.g. —CO—OR$^1$ (R$^1$ may be an alkyl group having about 1 to 6 carbon atoms)]. Examples of the irreversibly dimerizable compound include 4-hydroxy chalcone, 4'-hydroxy chalcone, and 4,4'-hydroxy chalcone.

In order to allow a dimerizable compound to be introduced to a mesoporous silica, an olefin group may be introduced to the dimerizable compound, which then reacts with hydrosilanes to synthesize a silane compound containing a dimerizable group.

An olefin group can be introduced to a dimerizable compound, for example, by reacting an organic halide having an olefin group with a functional group such as the hydroxyl group of the dimerizable compound in a usual manner, for example, in a solvent and/or in the presence of a base. The organic halide having an olefin group may be, but not limited to, allyl chloride, allyl bromide, allyl iodide, 3-bromocyclohexene, or 6-bromo-1-hexene, which has about 3 to 8 carbon atoms. The kind (the number of carbon atoms) of the organic halide having an olefin group may appropriately selected depending on the kind of the compound having a dimerizable organic group, to allow the dimerizable compound to close the entrances of the pores of the mesoporous silica when dimerized.

The solvent may include acetone, methyl ethyl ketone, dimethylformamide, dimethylsulfoxide, tetrahydrofuran, and 1,4-dioxane. A particularly preferable solvent is acetone. The base may include sodium carbonate, potassium carbonate, potassium bicarbonate, sodium bicarbonate, sodium hydroxide, potassium hydroxide, potassium hydroxide, cesium carbonate, sodium methoxide, and potassium-t-butoxide. The amount of the base to be used may be 1 to 3 molar equivalents with respect to a dimerizable compound such as 7-hydroxycoumarin. The reaction temperature may be about 40 to 100° C., preferably 60 to 80° C. The reaction time may be about 3 to 24 hours.

The obtained olefin-containing dimerizable compound is reacted with alkoxysilane in a usual manner to provide a silane compound containing a dimerizable group. While alkoxysilane to be used herein may be a compound having at least one alkoxy group, preferably alkoxysilane represented by $HSiR_3$ (in this formula, R may be the same or different, and represents an alkyl group having about 1 to 4 carbon atoms or an alkoxy group having about 1 to 3 carbon atoms, wherein at least one of R is an alkoxy group having 1 to 3 carbon atoms), the present invention is not limited to such a compound, but any other suitable compound capable of reacting with a silanol group of the hexagonal mesoporous silica to introduce a dimerizable functional group to the hexagonal mesoporous silica may be used. Specifically, the alkoxysilane may include triethoxysilane, trimethoxysilane, diethoxymethylsilane, and ethoxydimethylsilane.

The above reaction may be conducted in the presence of a solvent and/or a catalyst. The solvent may include toluene, xylene, tetrahydrofuran, dioxane, benzene, hexane, dichloromethane, and chloroform. A particularly preferable solvent is toluene or xylene. The amount of the dimerizable compound to be used is preferably about 1 to 1.5 molar equivalents, more preferably about 1 to 1.2 molar equivalents, with respect to the alkoxysilane. The catalyst may include: a platinum catalyst, such as platinum-1,3-divinyl-1,1,3,3-tetramethyldisiloxane complex, platinum-2,4,6,8-tetramethyl-2,4,6,8-tetravinylcyclotetrasiloxane complex, chloroplatinic acid, activated carbon-bearing platinum, and alumina-bearing platinum; a rhodium catalyst, such as Wilkinson's complex $(RhCl(PPh_3)_3)$, activated carbon-bearing rhodium, and alumina-bearing rhodium; and a palladium catalyst, such as tetrakistriphenylphosphine palladium, and activated carbon-bearing palladium. The amount of the catalyst to be used may be about 0.005 to 0.5 mol %, preferably about 0.02 to 0.1 mol % with respect to the alkoxysilane. The reaction temperature may be about 0 to 80° C., preferably about 25° C. to 30° C. The reaction time-period may be 10 minutes to 4 hours.

The obtained dimerizable-group-containing silane compound is introduced to the hexagonal mesoporous silica having the template surfactant filled in the pores thereof instead of the hexagonal mesoporous silica from which the template surfactant has been removed through calcination or extraction. Thus, the template surfactant filled in the pores allows the dimerizable-group-containing silane compound to be introduced to the hexagonal mesoporous silica in such a manner that it reacts with only the silanol group at the entrances of the pores without entering into the pores.

The dimerizable functional group can be introduced to the pore entrances of the mesoporous silica by suspending the hexagonal mesoporous silica in a solvent (e.g. n-hexane, or toluene), and then adding a dimerizable-group-containing silane compound to react with the hexagonal mesoporous silica at a temperature of about 25° C. to 80° C. for about 10 minutes to 6 hours.

While the amount of the dimerizable-group-containing silane compound to be used may be typically about 2 to 20 weight parts on the basis of 100 weight parts of the mesoporous silica filled with the temperate surfactant, the present invention is not limited to such a specific value, but any other suitable value allowing the silane compound to confine the functional substance to be incorporated into (filled in) the pores of the hexagonal mesoporous silica when dimerized after the introduction may be selected.

In addition, the photo-dimerizable functional group may be introduced to the hexagonal mesoporous silica so as to form a linkage capable of being readily split, such as ester linkage, amide linkage or disulfide linkage, by causing a reaction between the silanol group at the pore entrances of the hexagonal mesoporous silica and the dimerizable functional group through a suitable conventional method depending on the kind of the photo-dimerizable compound. In this case, the dimerized functional group may be split through an appropriate method such as acid treatment or a reduction reaction.

[III] Removal of Surfactant

After the introduction of the dimerizable functional group to the mesoporous silica, the surfactant remaining in the pores is removed with a solvent. In this process, if the remaining surfactant is removed through a calcination treatment, the introduced dimerizable functional group will be eliminated. Thus, in the method of the present invention, it is essential to remove the remaining surfactant with a solvent.

The surfactant is preferably removed, but not limited to, through an extraction-method using alcohol (e.g. aliphatic alcohol, such as methanol or ethanol) capable of adequately dissolving the surfactant. When alcohol is used, the surfactant is preferably removed with a mixture of hydrochloric acid and alcohol. When hydrochloric acid is used, the concentration of the hydrochloric acid in the mixture is preferably, but not limited to, about 0.5 to 5 M.

In the mesoporous silica with a hexagonal structure obtained in this manner, the mesoporous silica having a dimerizable organic functional group at the pore entrances is also encompassed within the scope of the present invention.

The term "dimerizable organic functional group" in the mesoporous silica means that the organic functional group has not been dimerized yet, and the pore entrances of the mesoporous silica are still open. The term also means that the organic functional group has been introduced to the pore entrances of the mesoporous silica, but not substantially introduced into or to the inside of the pores. More specifically, the term means that the dimerizable organic functional group has been introduced to a position of the mesoporous silica where the functional group can close the pore entrances when dimerized.

[IV] Filling of Functional Substance and Dimerization of Dimerizable Functional Group In the dimerizable functional group-introduced mesoporous silica synthesized as above, the functional group can be dimerized to cover and close the pore entrances of the mesoporous silica.

The dimerization can be caused by irradiation of the mesoporous silica with light, such as ultraviolet light having a wavelength depending on the kind of the functional group. The irradiation time may be appropriately set depending on the amount of the functional group to be dimerized. For example, it may be set in accordance with the measurement of the absorption peak of the dimerizable functional group.

When a reversibly photo-dimerizable group such as a coumarin derivative is introduced as a dimerizable compound, the dimerization can be typically caused by irradiating the mesoporous silica with ultraviolet light having a wavelength of 310 nm or more, particularly about 320 nm to 340 nm. While a lamp to be used herein is preferably a high-pressure mercury lamp, the present invention is not limited to such a specific lamp, but any other suitable lamp capable of radiating ultraviolet light having a wavelength of 310 nm or more. When a high-pressure mercury lamp is used, light components having a wavelength of less than 310 nm can be removed by radiating light through a heat-resistant hard glass jacket. When a coumarin derivative is used as a dimerizable functional group, the dimerized functional group can be split and monomerized by irradiating the mesoporous silica with ultraviolet light having a wavelength of about 250 nm (e.g. about 240 to 260 nm). The ultraviolet light of this wavelength can be radiated by using a low-pressure mercury lamp together with a silica or quartz glass housing. This reversible change can be determined by measuring the presence of ultraviolet absorption (absorption at about 310 to 330 nm when the photo-dimerizable group is a coumarin derivative) in an ultraviolet spectrum of the photo-dimerizable group.

The dimerization/monomerization reactions of reversibly dimerizable group such as coumarin derivatives can be utilized to on-off control the function of controllably releasing a functional substance incorporated in the pores of the mesoporous silica to the outside of the pores. Specifically, a functional substance can be released in any desired place at any desired amount by irradiating the mesoporous silica with light having a wavelength causing the split of dimerized organic functional group to allow the functional substance to be released to the outside of the pores and with light having a wavelength causing the dimerization of the organic functional group to allow the release of the functional substance to be discontinued. Further, the above on-off control can be repeated.

When the dimerized group cannot be split by light, it may be split by other means depending on the type of the linkage between the group and the mesoporous silica. For example, an ester linkage, amide linkage or disulfide linkage can be split through a hydrolysis reaction using an acid or the like, or a reduction reaction to allow the functional substances to be released to the outside of the pores. Thus, even if the group is associated with the mesoporous silica through an irreversible linkage, the release of the functional substance confined in the pores can be on-off controlled at any desired place or when needed.

Any functional substance capable of getting into the pores may be selectively used as the substance to be filled in the pores of the mesoporous silica, according to intended purposes. A method of filling the functional substance in the pores can be appropriately selected in consideration of the kind of the functional substance and other factors. For example, the mesoporous silica of the present invention having the un-dimerized functional group (off state) may be immersed into a liquid containing a functional substance to introduce the functional substance into the pores, and then the functional group may be dimerized to close the pore entrances.

The filling method will be described in more detail below in connection with a specific example in which a coumarin derivative is used as the dimerizable group, and cholestane, a steroid, is used as the functional substance.

A mesoporous silica modified with the organic functional group consisting of a coumarin derivative is immersed (for about 24 hours) in an n-hexane solution containing cholestane (the concentration of cholestane and the amount of the solution are not limited to a specific value). Then, the mesoporous silica is filtered and sufficiently rinsed with n-hexane. The mesoporous silica containing cholestane is irradiated with ultraviolet light from a high-pressure mercury lamp through a heat-resistant hard glass jacket to remove the light having a wavelength of less than 310 nm. The irradiation time may be appropriately set according to the amount of the mesoporous silica. The irradiation is continued until there shows no reduction in absorption of the photo-dimerizable group in measured ultraviolet spectrum.

The mesoporous silica can be irradiated with ultraviolet light of about 250 nm wavelength from a low-pressure mercury lamp with a silica glass housing to split the dimerized functional group and release (controllably release) the functional substance. In this case, the irradiation time may be appropriately set according to the amount of the functional substance (cholestane) to be controllably released to allow the irradiation to be discontinued when there shows no increase in absorption of the photo-dimerizable group in measured ultraviolet spectrum.

The mesoporous silica of the present invention has a function of incorporating a functional substance in its solid body and releasing (controllably releasing) the functional substance from the inside to the outside of the solid body. That is, the mesoporous silica of the present invention has a function of supplying a functional substance in a desired amount only when needed according to circumstances. The mesoporous silica of the present invention can be used in various fields (e.g. medicines, agricultural chemicals, cosmetics, catalysts, fertilizers and aroma chemicals). For example, it is contemplated to use the mesoporous silica of the present invention in combination with an odor sensor of ambient air to controllably release an incorporated aromatic compound to the outside in response to the detection of odor so as to maintain comfortable ambient air, or it is activated to apply agricultural chemicals in response to the arrival of harmful insects. It is also contemplated to use it as a drug delivery system in such a manner that a mesoporous silica incorporating a drug therein is injected into a human body, and then only an affected area is irradiated with ultraviolet light to allow the drug to act only in the affected area. It is also expected to use it in such a manner that when the concentration of a chemical substance in surrounding air increases up to a given value, a dimerized functional group is split so as to absorb the chemical substance into the pores thereof to remove the chemical substance from the surrounding air.

As described above, the present invention provide a hexagonal mesoporous silica modified with an organic functional group reversibly or irreversibly dimerizable in response to light irradiation such as ultraviolet irradiation. This mesoporous silica allows the functional substance incorporated in the pores thereof to be controllably diffused to the outside of the pores in response to ultraviolet irradiation or the like.

While the present invention will be more specifically described below in conjunction with Examples, it is not limited thereto.

EXAMPLE 1

Synthesis of Hexagonal Mesoporous Silica (Containing Template Surfactant)

22.86 g of sodium silicate (silicon: 0.20 mol; sodium: 0.184 mol) was completely dissolved in 100 g of water 48.86 g of tetramethylammonium hydroxide (0.134 mol) and 38.72 g of hexadecyltrimethylammonium bromide (0.102 mol) were added to another 100 g of water, and completely dissolved therein by heating them up to 35° C. The two homogenous aqueous solutions were mixed together, and sufficiently stirred at about 25° C. for 2 hours.

Then, 13.28 g of sulfuric acid (0.13 mol) dissolved in 51 g of water was slowly added to the above solution, and the obtained mixed solution was stirred at about 25° C. for 2 hours to form a precipitate. The solution part of the mixed solution had a pH of about 10.5. The mixed solution was transferred into a polypropylene bottle, and left at 100° C. for 24 hours. After the mixed solution was cooled down to about 25° C., concentrated sulfuric acid was added thereto until the pH become about 10.5. Then, 11.83 g of potassium chloride (0.15 mol) was added thereto, and the obtained solution was left at 100° C. for 24 hours. After that, concentrated sulfuric acid was added again to adjust the pH to about 10.5. The precipitate formed was filtered, and sufficiently rinsed with distilled water. Then, the precipitate was dried at 105° C. for 24 hours. In this manner, a hexagonal mesoporous silica containing a template surfactant was synthesized with a stable structure.

Synthesis of 7-allyloxycoumarin 4.15 g (30 mmol) of potassium carbonate anhydride (insoluble) and subsequently, 6.05 g (50 mmol) of allyl bromide were added to an acetone solution (100 mL) containing 3.24 g of commercially available 7-hydroxycoumarin (20 mmol). The obtained solution was reacted at 70° C. for 12 hours. After filtering out an insoluble matter, the reaction solution was distilled under reduced pressure to obtain 4.02 g of residue (crude yield; 99%). The obtained solid material was recrystallized with ethanol to obtain 3.85 g of 7-allyloxycoumarin compound (yield; 95%). The following analysis data of the obtained compound were obtained.

$^1$H NMR (CDCl$_3$, 400 MHz): 4.60 (d, 2H), 5.49 (dd, 1H), 6.0–6.08 (m, 1H), 6.24 (d, 1H), 6.85 (d, 1H), 6.86 (dd, 1H), 7.38 (d, 1H), 7.64 (d, 1H) ppm. Infrared spectrum (KBr method) (primary absorptions): 3082, 1726, 1615, 1285, 1228, 1128, 1127, 998, 843 cm$^{-1}$.

Preparation of 3-(7-coumariloxy) propyltriethoxysilane 2.02 g (10 mmol) of 7-allyloxycoumarin and 1.80 g (11 mmol) of triethoxysilane were dissolved in 50 mL of toluene, and dry nitrogen was blown thereinto for 10 minutes. Then, the obtained solution was added with 0.5 mL of catalyst solution (2 mM platinum-1,3-divinyl-1,1,3,3-tetramethyldisiloxane complex solution in toluene), and reacted therewith at about 25° C. for 20 hours. After the solvent (toluene) was removed through distillation under reduced pressure, the obtained oily product was dried under reduced pressure to obtain a crude target material (3.45 g; crude yield 95%). This crude product was directly used in the next synthesis (Example 1-(4) described below). The following analysis data of the obtained compound were obtained.

$^1$H NMR (CDCl$_3$, 400 MHz): 0.75 (dd, 2H), 1.23 (t, 9H), 1.80–1.95 (m, 2H), 3.78 (q, 6H), 4.00 (t, 2H), 6.23 (d, 1H), 6.80–6.90 (m, 2H), 7.35 (d, 1H), 7.63 (d, 1H) ppm, $^{13}$C NMR (CDCl$_3$, 99 MHz): 9.97, 18.39, 22.61, 58.12, 70.58, 101.22, 112.23, 112.73, 112.79, 128.56, 143.29, 155.71, 161.05, 162.16 ppm.

Infrared spectrum (KBr method) (primary absorptions): 2970, 1736, 1616, 1124, 1078 cm$^{-1}$.

Synthesis of Coumarin Derivative-derived Organic Functional Group-introduced Mesoporous Silica 2 g of the mesoporous silica prepared in above (1) was suspended in 20 mL of n-hexane. Then, the suspension was added with 0.2 g of 3-(7-coumariloxy) propyltriethoxysilane, and stirred at about 25° C. for 30 minutes. After removing the solvent through distillation under reduced pressure at 80° C. for 2 hours, the obtained material was vacuum-dried at 150° C. for 12 hours. The template (surfactant) remaining in the obtained coumarin derivative-derived organic functional group-contained mesoporous silica was removed by refluxing therethrough 100 mL of ethanol containing 1 M hydrochloric acid at 80° C. for 4 hours. Then, the supernatant liquid was removed, and the solid material was re-subjected to reflux treatment using the same ethanol solution. After repeating the reflux treatment three times, the solid material was filtered, sufficiently rinsed with ethanol, and then dried at 80° C. for 12 hours. The results of gas chromatography, thermogravimetry, and elemental analysis proved that the template surfactant was completely removed.

On-off Control of Controlled-release of Cholestane Using Coumarin Derivative-derived Organic Functional Group-introduced Mesoporous Silica 1 g of coumarin derivative-derived organic functional group-introduced mesoporous silica was suspended at about 25° C. for 24 hours in 20 mL of n-hexane solution containing 1 g of cholestane dissolved therein. The mesoporous silica was filtered, rinsed 5 times with n-hexane, and dried at 60° C. for 12 hours. The amount of cholestane remaining in the mesoporous silica was calculated from the amount of cholestane in n-hexane used in the rinsing. As a result, it was verified that 33.0% by weight of cholestane was incorporated in the mesoporous silica.

Using a high-pressure mercury lamp, the solid body itself of the cholestane-incorporated mesoporous silica was irradiated for 3 hours with ultraviolet light in which light components of less than 310 nm of wavelength is removed by a heat-resistant hard glass jacket. Then, the mesoporous silica was re-suspended in 20 mL of n-hexane, and sufficiently stirred at about 25° C. for 24 hours. Subsequently, the solid material was filtered, and rinsed with a sufficient amount of n-hexane. All the filtered solution and the rinsing solutions were combined, and subjected to gas chromatography to determine the quantity of eluted cholestane. The detected cholestane was 6%. That is, 27% of cholestane was still left in the solid material.

The solid body itself of the mesoporous silica was irradiated for about 5 minutes with ultraviolet light having a wavelength of about 240 to 260 nm using a low-pressure mercury lamp with a silica glass housing. Then, the mesoporous silica was re-suspended in 20 mL of n-hexane, and sufficiently stirred at about 25° C. for 48 hours. Subsequently, the solid material was filtered, and rinsed with a sufficient amount of n-hexane. The filtered solution and the rinsing solutions were combined, and subjected to gas chromatography to determine the quantity of eluted cholestane. The incorporated cholestane was 10%. That is, 17% of cholestane was eluted.

Comparative Example 1

Controlled-release of Cholestane Using Mesoporous Silica Devoid of Dimerizable Functional Group The surfactant was removed from the mesoporous silica obtained in Example 1-(1), using ethanol containing hydrochloric acid in the same manner as in Example 1-(4). This mesoporous silica was suspended at about 25° C. for 24 hours in 20 mL of n-hexane solution having 1 g of cholestane dissolved therein. The mesoporous silica was filtered, and rinsed 5 times with n-hexane. Then, the mesoporous silica was dried at 60° C. for 12 hours.

After the cholestane was incorporated in the mesoporous silica in this manner, the mesoporous silica was re-suspended in 20 mL of n-hexane, and sufficiently stirred at about 25° C. for 24 hours. Then, the solid material was filtered, and rinsed with another sufficient amount of n-hexane. The filtered solution and the rinsing solutions were combined, and subjected to gas chromatography to determine the quantity of the eluted cholestaine. Most of the initial cholestane was eluted in n-hexane, and the amount of the remaining cholestane was 2% or less.

Comparative Example 2

Controlled-release of Cholestane Using Coumarin Derivative-derived Organic Functional Group-introduced Mesoporous Silica Without Light Irradiation The coumarin derivative-derived organic functional group-introduced mesoporous silica obtained in Example 1-(4) was suspended in 20 mL of n-hexane solution having 1 g of cholestane dissolved therein, at about 25° C. for 24 hours. The mesoporous silica was filtered, and rinsed 5 times with n-hexane. Then, the mesoporous silica was dried at 60° C. for 12 hours.

Without ultraviolet irradiation, the mesoporous silica was directly suspended in 20 mL of n-hexane, and sufficiently stirred at about 25° C. for 24 hours. Then, the solid material was filtered, and rinsed with sufficient amount of n-hexane. The filtered solution and the rinsing solutions were combined, and subjected to gas chromatography to determine the quantity of the eluted cholestaine. Most of the initial cholestane was eluted in n-hexane, and the amount of the remaining cholestane was 2% or less.

EXAMPLE 2

On-Off Control of Controlled Release of Pyrene Using Coumarin Derivative-derived Organic Functional Group-introduced Mesoporous Silica The controlled release of a functional substance was on-off controlled in the same manner as that in Example 1 except that 1 g of pyrene was used as a substance to be incorporated as a substitute for cholestane. After the mesoporous silica is irradiated with ultraviolet light using a high-pressure mercury lamp, and rinsed with n-hexane, 1.05% (by weight) of pyrene was incorporated in the mesoporous silica on the basis of 100% of the mesoporous silica. After the mesoporous silica is irradiated using a low-pressure mercury lamp, and rinsed with n-hexane, 0.28% (by weight) of pyrene was incorporated in the mesoporous silica on the basis of 100% of the mesoporous silica.

Comparative tests were conducted in the same manner as that in Comparative Examples 1 and 2 except that 1 g of pyrene was used as a substance to be incorporated as a substitute for cholestane. In either test, after the mesoporous silica was rinsed with n-hexane, 0.00% of pyrene was incorporated in the mesoporous silica.

As seen in the results of Examples 1, 2 and Comparative Examples, when the dimerizable organic group is photo-dimerized with ultraviolet irradiation, the incorporated functional substance (cholestane and pyrene) will not be controllably released even if the mesoporous silica is rinsed with a solvent for the functional substance. On the other hand, the incorporated functional substance (cholestane and pyrene) can be controllably released by irradiating the mesoporous silica with ultraviolet light of a shorter wavelength and monomerizing the dimerized organic group. That is, the controlled-release of the incorporated substance could be on-off controlled by use of light. In particular, coumarin can be reversibly dimerized in response to light, which desirably allows the on-off control function to be repeated.

Although the invention has been described with respect to specific embodiments, the details are not to be construed as limitations, for it will become apparent that various embodiments, changes and modifications may be resorted to without departing from the spirit and scope thereof, and it is understood that such equivalent embodiments are intended to be included within the scope of this invention.

What is claimed is:

1. A mesoporous silica having a hexagonal structure, comprising an organic functional group provided at the entrances of the pores thereof, said organic functional group being dimerizable in response to light.

2. The mesoporous silica as defined in claim 1, wherein said organic functional group is an $\alpha$, $\beta$-unsaturated ketone moiety.

3. The mesoporous silica as defined in claim 1, wherein said organic functional group is reversibly dimerizable in response to light.

4. The mesoporous silica as defined in claim 1, wherein said organic functional group is derived from a coumarin derivative.

5. A mesoporous silica having a hexagonal structure, comprising a functional substance filled in the pores thereof, and a dimerized organic functional group provided at the entrances of said pores to close said entrances,
    wherein said organic functional group is reversibly dimerizable in response to light.

6. The mesoporous silica as defined in claim 5, wherein said organic functional group is an $\alpha$, $\beta$-unsaturated ketone moiety.

7. The mesoporous silica as defined in claim 5, wherein said organic functional group is derived from a coumarin derivative.

8. A method of producing a mesoporous silica, comprising the steps of:
    (1) preparing a mesoporous silica having a hexagonal structure by use of a template comprising a surfactant capable of forming a hexagonal structure in an aqueous solution;
    (2) introducing an organic functional group to said mesoporous silica having a hexagonal structure while leaving the surfactant in the pores of said mesoporous silica, said organic functional group being dimerizable in response to light; and
    (3) removing the surfactant contained in said mesoporous silica with a solvent.

9. The method as defined in claim 8, which comprising the step of subjecting said mesoporous silica to acid treatment, between said preparing step (1) and said introducing step (2).

10. A method of producing a mesoporous silica, comprising the steps of:
    (1) preparing a mesoporous silica having a hexagonal structure by use of a template comprising a surfactant capable of forming a hexagonal structure in an aqueous solution;
    (2) introducing an organic functional group to said mesoporous silica having a hexagonal structure while leaving the surfactant in the pores of said mesoporous silica, said organic functional group being dimerizable in response to light;
    (3) removing the surfactant contained in said mesoporous silica with a solvent;
    (4) filling the pores of said mesoporous silica with a functional substance; and
    (5) dimerizing said organic functional group with light.

11. The method as defined in claim 10, further comprising the step of subjecting said mesoporous silica to acid treatment between said preparing step (1) and said introducing step (2).

12. A method of removing a chemical substance, comprising the steps of:
    preparing a mesoporous silica having a hexagonal structure, comprising an organic functional group provided at the entrances of the pores thereof, said organic functional group being dimerizable in response to light;
    incorporating the chemical substance into the pores of said mesoporous silica; and
    dimerizing said organic functional group with light.

13. A method of controlling release of a functional substance, comprising the steps of:

preparing a mesoporous silica having a hexagonal structure, comprising the functional substance filled in the pores thereof, and a dimerized organic functional group provided at the entrances of said pores to close said entrances; and splitting said dimerized organic functional group to allow said functional substance to be released from said pores.

14. A method of controlling release of a functional substance, comprising the steps of:

preparing a mesoporous silica having a hexagonal structure, comprising the functional substance filled in the pores thereof, and a dimerized organic functional group provided at the entrances of said pores to close said entrances, wherein said organic functional group is reversibly dimerizable in response to light; and irradiating said mesoporous silica with a light having a wavelength causing split of said dimerized organic functional group to allow said functional substance to be released from said pores.

15. The method of controlling release of a functional substance as defined in claim 14, further comprising a step of:

irradiating said mesoporous silica with a light having a wavelength causing dimerization of said organic functional group to allow the release of said functional substance to be discontinued.

* * * * *